United States Patent [19]

Falcetta et al.

[11] Patent Number: 4,690,993
[45] Date of Patent: Sep. 1, 1987

[54] P-(2-HYDROXY HEXAFLUOROISOPROPYL) STYRENE [HFIS] MONOMER FOR OPHTHALMIC APPLICATIONS

[75] Inventors: Joseph J. Falcetta; Joonsup Park, both of Arlington, Tex.

[73] Assignee: Alcon Laboratories, Inc., Forth Worth, Tex.

[21] Appl. No.: 815,439

[22] Filed: Dec. 31, 1985

Related U.S. Application Data

[63] Continuation-in-part of Ser. No. 801,259, Nov. 25, 1985.

[51] Int. Cl.$^4$ .................. C08F 212/20; C08F 230/08
[52] U.S. Cl. .................... 526/242; 526/279; 523/106; 523/107
[58] Field of Search ............... 526/279, 242; 523/106, 523/107

[56] References Cited

U.S. PATENT DOCUMENTS

| Re. 31,406 | 10/1983 | Gaylord | 526/279 |
|---|---|---|---|
| 3,179,640 | 4/1965 | Middleton | 260/85.5 |
| 4,139,548 | 2/1979 | Tanaka et al. | 260/448.2 B |
| 4,152,508 | 5/1979 | Ellis et al. | 526/279 |
| 4,153,641 | 5/1979 | Diechert et al. | 260/827 |
| 4,372,203 | 4/1982 | Diechert et al. | 526/279 |
| 4,424,328 | 3/1984 | Ellis | 526/279 |
| 4,433,111 | 2/1984 | Tighe et al. | 523/106 |
| 4,450,264 | 5/1984 | Cho | 526/279 |
| 4,540,761 | 9/1985 | Kawamura et al. | 526/279 |

Primary Examiner—Joseph L. Schofer
Assistant Examiner—Peter F. Kulkosky
Attorney, Agent, or Firm—James Arno; Gregg C. Brown

[57] ABSTRACT

Copolymer compositions are prepared from a novel class of siloxane monomers in combination with hydroxyperfluoroalkylstyrenes, preferably p-(2-hydroxy hexafluoroisopropyl)sytrene [HFIS] monomer for ophthalmic applications.

7 Claims, No Drawings

P-(2-HYDROXY HEXAFLUOROISOPROPYL) STYRENE [HFIS] MONOMER FOR OPHTHALMIC APPLICATIONS

CROSS REFERENCE TO A RELATED APPLICATION

This application is a continuation-in-part of co-pending, commonly assigned application of Park and Falcetta, Ser. No. 801,259, filed Nov. 25, 1985, and entitled NEW SILOXANE MONOMERS FOR OPHTHALMIC APPLICATIONS.

BACKGROUND OF THE INVENTION

The present invention relates to a copolymer composition which employs a class of novel siloxane monomers containing both an aromatic ring and vinyl functionality, as a monomer for preparing copolymers in combination with p-(2-hydroxy hexafluoroisopropyl)styrene (HFIS). Copolymers comprising variable amounts of the monomers are transparent to visible light, have a high refractive index, and are useful, inter alia in fabricating lenses, especially contact lenses and intracameral devices such as corneal inserts and intraocular implants. Contact lenses comprise generally fillerless, oxygen transportable hydrolytically stable, biologically inert, transparent plastic bodies which are prepared from polymerization, or copolymerization of monomers. The novel class of siloxane monomers containing both an aromatic ring and vinyl functionality are the subject of our copending commonly assigned application, Ser. No. 801,259, filed Nov. 25, 1985, now U.S. Pat. No. 4,633,003 Park and Falcetta, and entitled NEW SILOXANE MONOMERS FOR OPHTHALMIC APPLICATIONS. The copolymers of this invention which contain this monomer are optically clear and colorless.

The polymers and copolymers described herein can be usefully employed for making "hard" or "soft" contact lenses, intraocular implants, intracorneal implants, semisoft contact lenses, as well as in other biomedical applications. Importantly, the copolymers of this invention, that is the combination of the novel class of siloxane monomers of Ser. No. 801,259 and HFIS, are especially adapted for, and suitable in, making hard gas permeable contact lenses, with the HFIS contributing to wettability without any negative impact on oxygen permeability. In fact, oxygen permeability is enhanced. The copolymers may also have other uses such as permeable films, etc., but the primary description given will emphasize lens utility.

Hard contact lenses have the advantages of excellent machinability, excellent stability, and excellent visual clarity. However, hard contact lenses have their disadvantages, as well. Generally for many, including the most common hard lenses, i.e. those made of polymethyl methacrylate (PMMA), oxygen permeability is low and the hydrophilic properties are poor.

It is important and essential that the cornea have access to atmospheric oxygen in order that an oxygen-carbon dioxide exchange can occur. Put another way, without constant eye exposure to the atmosphere, a state of oxygen edema can occur within the eye, which is potentially capable of causing damage. Thus, hard contact lenses, while having many practical advantages, generally are not altogether satisfactory because they most often have poor oxygen permeability.

A good hard contact lens would have not only excellent oxygen permeability, but also excellent tear-fluid wettability. Wettability is important in that if the lens is not wettable it cannot be comfortably worn in the eye. The patient will perceive the lens as uncomfortable and scratchy, absent good wettability.

Generally, in the past, polymer formulation for optical lens products has involved an initial determination as to whether one was formulating either a hard lens or a soft lens, followed by formula manipulation within a distinctly different class of monomers useful for one type, but not necessarily useful for the other. As explained in our co-pending earlier referenced application Ser. No. 801,259, it has now been found possible to make contact lenses, involving as a siloxane monomer ingredient of variable presence, a monomer which can be adapted for making either hard or soft lenses. In this present invention, the novel class of siloxane monomers is combined with a comonomer of preferred HFIS or other hydroxyfluoroalkylstyrene, which contributes both wettability and oxygen permeability.

Indeed, it is an object of the present invention to provide in combination with our earlier described class of novel siloxane monomers which have both an aromatic ring functionality and vinyl functionality at certain stereo-directing positions, a hydroxyfluoroalkylstyrene such as p-(2-hydroxy hexafluoroisopropyl)styrene (HFIS), resulting in copolymers useful as materials for making a wide variety of types of optical products, especially gas permeable contact lenses and ocular implants.

A further object of the invention is to provide a copolymer combination of the type specifically mentioned above which is not only of good oxygen permeability, but which is highly compatible with other monomers, and which, when copolymerized with other minor monomers provides wettability, without sacrificing oxygen permeability.

A still further object of the present invention is to provide hard gas permeable contact lenses which contain as a main ingredient of variable presence, the hereinafter defined combination of monomers of the present invention.

A still further object of the present invention is to provide hydroxyfluoroalkylstyrenes such as the preferred HFIS as a monomer for use in biomedical lens devices to improve wettability, without any significant impact on oxygen permeability.

A further object of the present invention is to provide a copolymerizable compound suited for preparing contact lenses which have good oxygen permeability, are machineable, and which can be used with or without other minor monomer modifiers for hard gas permeable contact lenses which can be comfortably worn.

A still further object of the present invention is to prepare a copolymer combination which can be copolymerized with or without other minor, modifying monomers to provide a copolymer useful for optical products, particularly gas permeable hard contact lenses, wherein the copolymer has a DK, i.e. oxygen permeability constant value within the range of from about 12 to about 70, and which also has a highly wettable surface. Such lenses are comfortable, when worn show no evidence of substantial corneal edema, are of good machineability, are dimensionally stable, are tear wettable, and as well have sufficient lipophilicity to optimally interact with tear fluid.

The method and means of accomplishing each of the above objectives, as well as others will become apparent from the detailed description of the invention which will follow hereinafter.

SUMMARY OF THE INVENTION

Certain siloxane monomers which contain both an aromatic ring functionality and vinyl functionality are combined with hydroxyfluoroalkylstyrenes, preferably HFIS. The siloxane monomers in combination with hydroxyfluoroalkylstyrenes such as HFIS provide copolymer combinations useful for making gas permeable hard contact lenses, and other optical products. The new copolymer combinations of the present invention provide excellent oxygen permeability without adversely impacting other desirable properties such as machineability, wettability, lipophilicity, and dimensional stability. Moreover, the copolymers are useful for making lenses which are substantially inert to the eye and transparent, provide good visual clarity and sharpness of image. The monomers may be used alone or in combination with other minor, modifying monomers. The invention also relates to the use of hydroxyfluoroalkylstyrenes such as HFIS in all types of polymer compositions useful for making biomedical devices, especially lenses of improved wettability without adverse impact of oxygen permeability.

DETAILED DESCRIPTION OF THE INVENTION

It has now been found that the above-mentioned objects, as well as others, can be obtained by a combination of the novel class of siloxane monomer compound of the incorporated by reference parent application Ser. No. 801,259, and a hydroxyfluoralkylstyrene, preferably p-(2-hydroxy hexafluoroisopropyl) styrene, hereinafter referred to as HFIS. The monomer compound of the parent application containing both an aromatic ring and vinyl functionality, has the following formula (I):

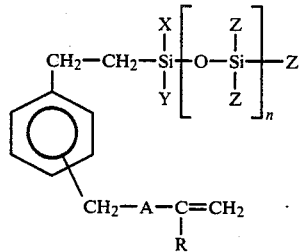

where
(1) "A" is selected from the group consisting of:

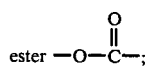

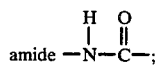

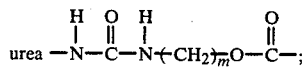

where m is a number and is from 2-4;
(2) R is hydrogen or methyl;

(3) X and Y are selected from the group consisting of $C_1$ to $C_5$ alkyl groups, phenyl groups and W groups;
(4) W is a group of the structure

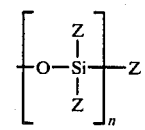

(5) Z is selected from the group consisting of $C_1$ to $C_5$ alkyl groups and phenyl groups; and
(6) n is an integer from zero to five.

It is not known precisely why the monomer of the parent application has a wide range of other monomer compatability, allowing it to be useful in making either hard or soft contact lenses, but it does. As explained in the parent application, without being bound to any theory, it is believed that perhaps its wide compatability is achieved because within the structure there is a synergistic relationship between the unique combination of functional groups and their spatial relationship to each other, giving the desirable properties. It is believed the presence of the aromatic ring contributes to a desirably higher index of refraction, on the order of 1.4515; the presence of the siloxane moiety provides for oxygen permeability; and, the presence of the vinyl functionality provides for good overall polymerization properties, without adversely impacting other desirable properties, especially oxygen permeability.

The novel siloxane monomer of the parent application, useful in the combination copolymer of this invention is prepared in a relatively straightforward, easy to perform, series of reactions, summarized by a synthetic scheme, starting with chloromethyl styrene, as depicted in the earlier referenced parent application Ser. No. 801,259. The synthesis need not, therefore, be repeated here.

The hereinafter description will be given with reference to the most preferred hydroxyfluoroalkylstyrene, HFIS, but it is to be understood that others coming within the scope of this invention may also be used. In accordance with this invention HFIS, or chemically p-(2-hydroxy hexafluoroisopropyl)styrene, may be added as a comonomer to other conventional monomer compositions in preparing a hard gas permeable lens of improved wettability. Importantly, the HFIS improves wettability without any significant adverse impact on oxygen permeability. The amount of HFIS employed may vary within the range of from about 10% by weight of the total monomer composition to about 60% by weight of the total monomer composition. In one preferred hard gas permeable lens composition of the present invention HFIS may be employed at the levels previously specified in combination with the novel class of siloxane monomers of the parent application, with the siloxane monomer being present at from about 25% by weight of the composition to about 50% by weight of the composition. Thus, the HFIS monomer of the present invention can be successfully employed as a monomer for preparing copolymers useful as a transparent material for gas permeable hard contact lenses, with or without being combined with the siloxane monomer invention of the parent application.

When the compound of the invention is copolymerized with other particular comonomers, there can be obtained copolymers suitable for use with contact lenses which have excellent oxygen permeability, affinity for the cornea, and can be continuously worn, long term, without giving a foreign body sensation. For instance as previously explained, when from about 25% by weight to about 50% by weight formula [I] siloxane monomer of the parent application invention is copolymerized with from about 10% by weight to about 40% by weight of a comonomer hydroxyflouroalkylstyrene compound, preferably HFIS, which also improves wettability, good polymeric compositions for hard gas permeable lenses result.

As those of ordinary skill in the art of polymer formulation for optical lens materials know, it is common to use other monomers at various levels of addition, besides the main comonomers in a composition. Those other formulation ingredients are herein referred to as minor modifying monomers. The term minor is from the standpoint of percentage in comparison with the amount of the siloxane monomer of formula I and the hydroxyfluoroalkylstyrene monomer such as HFIS in total, and does not mean minor in significance. In the lens modifications of this invention, minor modifying monomers may include from about 0% by weight to about 40% by weight of a compatible mechanical property modifier such as methyl methacrylate, tertiary butyl styrene or cyclohexyl methacrylate, from about 0% by weight to about 5% by weight of a hydrophilic wetting agent monomer such as methacrylic acid, and from about 0.5% by weight to about 2% by weight of a cross-linker such as ethyleneglycol dimethacrylate, an excellent hard gas permeable contact lens is achieved.

As those skilled in the art know, the copolymerization reactions mentioned herein typically occur in the presence of a radical polymerization initiator such as azobisisobutyronitrile or azobisdimethylvaleronitrile by means of a bulk polymerization reaction.

In one particularly preferred formulation for a hard gas permeable lens which has been found especially suitable, the lens formulation includes 35% of the penta-tris-siloxane monomer of the parent application, 10% of the tris-ureido siloxane monomer species of the parent application, 23% of HFIS, 30% of methylmethacrylate as a physical property modifier, and 2% of ethylene glycol dimethacrylate cross-linker.

Heretofore, particular reference has been made to the most preferred fluorostyrene monomer of the present invention, HFIS. It should be understood, however, that other fluorostyrenes generally of the types disclosed in U.S. Pat. No. 3,179,640 can be used herein. The disclosure of U.S. Pat. No. 3,179,640, patented Apr. 20, 1965, to the extent of its general description of fluorostyrene monomers, their formulas and their methods of preparation is specifically incorporated herein by reference. The styrenes shown in that patent have the following general formulation:

wherein X and Y are, individually, the same or different monovalent polyfluoroalkyl, including perfluoroalkyl, ω-hydroperfluoroalkyl and ω-chloroperfluoroalkyl, radicals, or jointly, a divalent perfluoroalkylene radical. There is, however, no disclosure of any utility of those monomers in the incorporated-by-reference U.S. Pat. No. 3,179,640 as useful in polymeric compositions for biomedical devices, in particular, as monomers or copolymers for use in preparation of ophthalmic lenses, and in particular contact lenses. The preferred alkyl group is $C_1$ to $C_8$, and most preferred is $C_1$ to $C_3$.

The monomer, p-(2-hydroxy hexafluoroisopropyl)stryene [HFIS] has been described in U.S. Pat. No. 3,179,640 as a monomer which yields polymers having unusual swelling properties. Thus, while the monomer has been known for many years it has never been used in biomedical applications and specifically in ophthalmic applications. It has the formula:

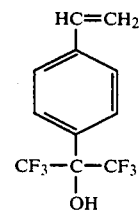

The following properties of HFIS make it the most preferred hydroxyfluoroalkylstyrene compound for use in copolymers intended for biomedical applications and specifically for ophthalmic applications in accordance with this invention. The pKa of HIFS is ~5.5 compared to the ~4.8 found with acrylic acid type comonomers. The index of refraction ($n_D{}^{25}$) of HFIS is 1.4577 compared to 1.4290 for methacrylic acid. The oxygen permeability (DK) of the homopolymer is $2.3 \times 10^{-11}$. The presence of the fluorine substituents may significantly reduce interaction with biological fluids such as tears. The homopolymer has a contact angle of 18° as measured by the captive bubble technique, which compares with contact angle of 37° under the same conditions for a commercial gas permeable hard lens.

Using HFIS one can obtain wettable polymers containing no methacrylic acid or a substantially reduced amount of methacrylic acid. These copolymers will have an improved oxygen permeability over copolymers containing methacrylic acid. A further desirable feature is that for given optical parameters, a thinner contact lens can be made due to the higher index of refraction of HFIS containing copolymers. This is advantageous since thinner contact lenses have improved physiological response and improved oxygen transport.

Generally, characterization of a contact lens as hard or soft will depend upon the minor modifying monomers polymerized with the hydroxyfluoroalkylstyrene monomers of the present invention. Other hydrophilic comonomers which may be incorporated to provide increased wettability, such as alkoxyacrylates. Other comonomers useful for making hydrogel type soft lenses and hard lenses include the hydroxy alkyl acrylates and methacrylates; hydroxyethyl methacrylate (HEMA), hydroxyethyl acrylate, hydroxy-polyethoxy ethyl methacrylate and the like. Examples of another class of suitable hydrophilic monomers are the N-vinyl heterocyclic monomers, suitable examples of such monomers being N-vinyl-2 pyrrolidone, N-vinyl pyridine and N-vinyl-ε-caprolactam. Also another class of hydrophilic monomers are the polymerizable olefinic acids and amides; suitable examples being acrylic acid, methacrylic acid, itaconic acid, fumaric acid, maleic acid, crotonic acid, acrylamide, methacrylamide and N-(1,1-dimethyl-3-oxobutyl acrylamide). Another suitable group of hydrophilic monomers are the lower alkyl vinyl ethers such as methyl and ethyl vinyl ether.

Other compatible mechanical property modifying monomers can be utilized to change the softening temperature and hardness and to improve machineability of the copolymer. Generally, these are somewhat hydrophobic monomers and preferred are the olefinically unsaturated polymerizable monomers with one polymerizable double bond per molecule. Suitable examples of such monomers are the linear or branched $C_1$ to $C_{10}$ alkyl esters of acrylic and methacrylic acid such as methyl acrylate, ethyl acrylate, butyl acrylate, 2-ethylhexyl acrylate, methyl methacrylate, ethyl methacrylate, butyl methacrylate, cyclohexyl methacrylate, 2-ethylhexyl methacrylate, 2-ethoxyethyl methacrylate, and the like monomers. Examples of other suitable hydrophobic monomers useful as compatible mechanical property modifiers are the vinyl ethers such as butyl vinyl ether and vinyl acetate, vinyl chloride, vinyl propionate, isoprene, vinyl carbazole, and styrene monomers other than those defined above for the main monomer which are styrenes, including alkoxy styrenes, e.g., methoxy and ethoxy sytrene, halogenated styrenes, hydroxyalkyl styrenes, alkoxy alkyl styrenes, and polyalkoxyether sytrenes.

As heretofore mentioned, certain ranges of cross-linking monomers may also be employed. These may be used to harden the resulting copolymer or to improve machineability or stability, or both. Examples of suitable cross-linking monomers are divinyl benzene, di- and higher functionality of methacrylates and acrylates such as ethylene glycol dimethacrylate, tetraethylene glycol dimethacrylate, polyethylene glycol dimethacrylate, trimethylol propane trimethylacrylate, pentaerythritol tetramethacrylate, and allyl methacrylate, allyl itaconate, diallyl itaconate, diallyl adipate and methylenebisacrylamide. The foregoing examples of cross-linking monomers are merely illustrative, others may also be used, and all may be used individually, or in combination.

While preferred polymerized compositions of this invention would include a siloxane formula [I] monomer of our parent application, and typically one other compatible comonomer, a wetting agent and a cross-linking agent, other minor modifying ingredients may also be added in making suitable buttons or bonnets. Such minors include coloring agents, light absorbers, certain other mechanical properties such as plasticizers and the like, so long as those other materials do not adversely effect the desired properties of main copolymerizable monomers of the invention and lenses made therefrom. One does not have to use the formula [I] siloxane, and this invention broadly contemplates the hereinbefore described hydroxyperfluoroaklylstyrenes as wetting agent monomers in any lens formulations.

The contact lenses can be formed from the copolymer by any of the conventional lens lathing molding and/or polishing processes. For example, the polymers can be formed into rods which are cut into small cylinders or disks, often referred to as buttons or bonnets, from which the contact lens can be machined.

The wearing comfort of the contact lenses of the gas permeable hard lens type can be enhanced by the use of wellknown wetting solutions, cleaners, disinfectant solutions, comfort drops, and the like.

The invention will be further described in connection with the following examples which are given for purposes of illustration and should not be construed as limiting on the invention. All parts and percents referred to herein are on a weight basis.

EXAMPLES

Example 1

Synthesis of tris (trimethylsiloxy) silane-m,p-chloromethyl phenylethane

A catalyst solution is prepared by adding, with stirring, 23.8 g. of concentrated sulfuric acid to a solution of 11.6 g. of ethanol in 16.5 ml of distilled water.

To a 500 ml round bottom flask that is situated on an ice batch, a mixture of 43.6 g. (0.33 mole) of trimethylacetoxysilane and 27.4 g. (0.1 mole) of trimethoxysilane-m,p-chloromethyl) phenylethane is added. To this mixture 9.1 ml of the catalyst solution is added in a dropwise manner over a time period of 30 minutes.

The reaction mixture is vigorously stirred for three days at room temperature. After separation, the organic layer is neutralized with sodium bicarbonate, washed with water and dried over magnesium sulfate.

A yield of 31 g. (69.2%) of a slightly yellow liquid having an index of refraction of 1.4515 is obtained at 120°–135° C. (0.3–0.4 mm).

The identity of the compound was confirmed by the infrared spectrum and nmr spectrum [7.1 ppm (m,4H); 0.0 ppm (s,27H)].

Example 2

Synthesis of tris (trimethylsiloxy) silane(m,p-methacryloxymethyl)phenylethane

A mixture of 13.4 g. (3.0 mmole) and 3.6 g. (3.3 mmole) of sodium methacrylate in 150 ml of dimethylformamide was stirred at 125° C. for one hour. After cooling with an ice bath, 100 ml of distilled water was added. This reaction mixture was then extracted four times with 100 ml volumes of ethyl acetate. The combined organic layer is washed 3 times with 50 ml of a saturated sodium chloride solution and dried over anhydrous magnesium sulfate. After stripping off the low boiling components by vacuum distillation the final product was obtained at 120°–129° C. (0.1 mm) in a yield of 53.4%.

The identity of the compound was proven by the infrared spectrum and nmr spectrum [7.1 ppm (m,4H), 6.0 and 5.4 ppm (2 broad s,2H), 0.0 ppm (s,27H)].

Example 3

Synthesis of tris (pentamethyl disiloxy) silane(m,p-methacryloxymethyl)phenylethane [Penta Tris Styrene]

Using a procedure similar to that given in Examples 1 and 2, trimethoxysilane(m,p-chloromethyl) phenylethane was reacted with pentamethylacetoxy-disilane to form tris (pentamethyl disiloxy)-(m,p-chloromethyl) phenylethane in 44% yield. This compound was then reacted with sodium methacrylate in dimethylformamide solution to give a 83.9% yield of tris (pentamethyl disiloxy) silane-m,p-methacryloyloxymethyl phenylethane.

The identity of the compound was confirmed by the infrared spectrum; 1730 cm$^{-1}$ (C=O), 1640 cm$^{-1}$ (CH$_2$=), 1615 cm$^{-1}$ (aromatic) and 1070 cm$^{-1}$ (Si—O—) and nmr spectrum; 7.1 ppm (m,4H); 5.9 and 5.3 ppm (2 broad s,2H); 1.8 ppm (s,3H); 0.0 ppm (broad s,45H).

Example 4

Synthesis of trimethylsiloxy-dimethylsilane(m,p-methacryloxymethyl)phenylethane Trimethylsiloxyl-dimethylsilane(m,p-chloromethyl)-phenylethane was synthesized by the reaction of pentamethyldisiloxane and vinyl benzyl chloride in the presence of chloroplatinic acid. This compound was then reacted with sodium methacrylate in dimethylformamide using procedures similar to those given in Example 2 to form trimethylsiloxy-dimethylsilane (m-p-methacryloxymethyl)phenylethane in a 50.7% yield. [B.P. 102° C. (0.1 mm)].

The identity of the compound was confirmed by the infrared spectrum; 1730 cm$^{-1}$ (C=O), 1640 cm$^{-1}$ (CH$_2$=), 1615 cm$^1$ (aromatic) 1070 cm$^{-1}$ (Si—O—) and the nmr spectrum; 7.1 ppm (m,4H); 5.9 and 5.3 ppm (broad s,2H), 5,0 ppm (s,2H), 0 ppm (2s,15H).

Example 5

Synthesis of bis (trimethylsiloxy) methylsilane(m,p-methacryloxymethyl)phenylethane Using the procedure set forth in Example 4, bis (trimethylsiloxy) methyl(m,p-methacryloxymethyl)phenylethane was prepared in a yield of 54.7%. [B.P. 104°-124° C. (0.1-0.2 mm)].

The identity of the compound was confirmed by the infrared spectrum; 1730 cm$^{-1}$ (C=O), 1640 cm$^{-1}$ (CH$_2$=), 1070 cm$^{-1}$ (Si—O—) and the nmr spectrum; 7.1 ppm (m,4H); 5.9 and 5.4 ppm (2 broad S,5H), 5.0 ppm (s,2H), 1.8 ppm (s,3H), 0 ppm (2s,21H).

Example 6

Synthesis of Tris (trimethylsiloxy) silane(m,p-3-N-methacryloxymethylureido-1-N-methyl)phenylethane [Tris Urea]

Tris (trimethylsiloxy) silane(m,p-azidomethyl)phenyl ethane was prepared by the reaction of 17.9 g. (40 mmole) with 2.80 g. (44 mmole) of sodium azide in 100 ml of methanol under reflux for four hours. After evaporation and washing with 100 ml of distilled water the residue was extracted three times with 100 ml of distilled water the residue was extracted three times with 100 ml portions of ethyl acetate. The combined extracts were washed twice with 50 ml distilled water each time, dried over anhydrous magnesium sulfate and evaporated in vacuo. The reaction product was obtained in 96.6% yield (17.2 g.), b.p. 120°-125° C. (0.4 mm).

Tris (trimethylsiloxy) silane(m,p-aminomethyl)phenylethane was prepared by the catalytic hydrogenation of tris (trimethylsiloxy) silane(m,p-azidomethyl) phenylethane.

To a Parr hydrogenation apparatus (500 ml capacity) were added, 16.3 g. (36 mmole) of tris (trimethylsiloxy) silane(m,p-azidomethyl)phenylethane, 2.6 g. acetic acid, 250 ml isopropanol and 0.87 g. of 5% palladium/-charcoal. A cycle of hydrogenation at 5 psi for 15 min., evacuation and hydrogenation at 5 psi for 15 min. is repeated twice. The reaction mixture is filtered with the aid of Celite and the low boiling organics evaporated. The resulting liquid is treated with a 50:50 mixture of 5% aqueous sodium carbonate: ethyl acetate and the organic layer is then dried over anhydrous sodium sulfate. Vacuum distillation yields 10.8 g. (70.7% yield) of tris (trimethylsiloxy) silane(m,p-aminomethyl) phenylethane, b.p. 145°-155° C. (0.1 mm).

The identity of the compound was confirmed by the infrared spectrum; 3350 cm$^{-1}$ (NH$_2$), 1070 cm$^{-1}$ (Si—O) and nmr spectrum; 7.0 ppm (m,4H), 3.8 ppm (s,2H), 1.6 ppm (s,2H), 0 ppm (s,27H).

Compound tris (trimethylsiloxy) silane(m,p-aminomethyl) phenylethane was then prepared from the reaction of tris (trimethylsiloxy) silane(m,p-aminomethyl)phenylethane with isocyanoethyl methacrylate. Compound tris (trimethylsiloxy) silane(m,p-aminomethyl)phenylethane (22.0 g., 51 mmole) was reacted with 10.6 g. (68 mmole) of isocyanoethyl methacrylate in 110 ml methylene chloride in the presence of 2.5-diphenyl-p-benzoquinone as an inhibitor. The isocyanoethyl methacrylate is added dropwise over a period of 30 minutes with stirring while the reaction mixture is cooled by an ice bath. At the end of this time the ice bath was removed and the reaction proceeded at room temperature for an additional 5κ hours. Concentrated ammonium hydroxide (2 ml) is then added. The organic layer is then washed with 40 ml distilled water three times and dried over anhydrous magnesium sulfate. Silica gel column separation with ethyl acetate-hexane as the eluent yielded 19.4 g. (65.0%) of tris (trimethylsiloxy) silane(m,p-3-N-methacryloxymethylureido-1-N-methyl)phenylethane.

The identity of the compound was confirmed by the infrared spectrum; 3380 cm$^{-1}$ (NH), 1730 cm$^{-1}$ (C=O), 1580 cm$^{-1}$ (NHCO), 1070 cm$^{-1}$ (—Si—O) and the nmr spectrum; 7.0 ppm (m,4H), 5.8 and 5.3 ppm (2s,2H), 4.8 ppm (m,2H), 4.1 ppm (m,4H), 3.3 ppm (5,2H), 1.8 ppm (s,3H), 0 ppm (s,27H).

Example 7

Synthesis of tris (trimethylsiloxy) silane(m,p-N-methacrylaminomethyl)phenylethane Methacryloyl chloride (2.92 g., 28 mmole) is added dropwise over a period of thirty minutes to a solution of 10.0 g. (23 mmole) of compound tris (trimethylsiloxy) silane(m,p-aminomethyl)phenylethane and 2.83 g. (28 mmole) triethylamine in 100 ml of chloroform on an ice bath. A trace amount of 2,5-diphenyl-p-benzoquinone is added as an inhibitor. After the addition of methacryloyl chloride is complete, the ice bath is removed and the reaction continued for a total of six hours. Concentrated ammonium hydroxide (2 ml) is then added. The organic layer is then washed with 40 ml distilled water three times and dried over anhydrous magnesium sulfate. Vacuum distillation was then employed to obtain a 38% yield of tris (trimethylsiloxy) silane(m,p-N-methacrylaminomethyl)phenylethane [b.p. 170°-175° C. (0.15 mm)].

The identity of the compound was confirmed by the infrared spectrum; 3350 cm$^{-1}$ (NH), 1670 and 1640 cm$^{-1}$ (NHCO), 1070 cm$^{-1}$ (SI—O—) and nmr spectrum; 7.0 ppm (m,4H), 6.0 ppm (broad, 1H), 5.5 and 5.2 ppm (2 broad s,2H), 4.3 ppm (2s,2H), 1.8 ppm (s,3H), 0 pp, (s,27H).

Examples 8 through 10

Using the reactions described in Examples 1 through 7, the monomers shown in Table I were prepared:

TABLE I

| Example # | Monomer | nmr data |
| --- | --- | --- |
| 8 | bis (trimethylsiloxy)methylsilane-(m,p-N—methacryloylaminomethyl)phenylethane | 7.1 ppm (m,4H)<br>5.6 & 5.3 ppm (2s,2H) |
| 9 | bis (trimethylsiloxy) methylsilane(m,p-3-N—methacryloxyethylureido-1-N—methyl) phenylethane | 7.0 ppm (m,4H)<br>6.0 & 5.5 ppm (2s,2H)<br>4.8 (Broad D$_2$O exchangable)<br>4.2 & 4.1 ppm (2t,4H)<br>3.3 ppm (t,2H)<br>0 ppm (2s,21H) |
| 10 | tris (pentamethyldisiloxy) silane(m,p-3-N—methacryloxyethylureido-1-N—methyl) phenylethane | 7.0 ppm (m,4H)<br>5.9 & 5.7 ppm (2 broad s,2H)<br>1.8 ppm (s,3H) |

Examples 11 through 14

Copolymer Films

Films of the copolymers listed in Table II were prepared between (4×4 in.) glass plates. The glass plates were pretreated with dimethyldichlorosilane and hydrolyzed to silanize the surface. Masking tape is placed around the edges of a glass plate to control the film thickness (target thickness was usually 0.1 mm). The monomer mix was placed on a glass plate, the two plates secured together by means of a metal clip and the assembly placed in an oven at 50° C. for one and one half hour. At the end of this time the glass plate assembly was heated to 90° C. for an additional 90 minutes. The thin film was then removed from the glass plate assembly and stored in distilled water (phosphate buffer, pH 7.4). For all of the copolymers listed in Table II, 1.0 weight % of USP 245 (2,5-dimethyl-2,5-diperoxy-2'-ethylhexoate hexane) was added.

The composition of each copolymer in mole percent is: siloxane monomer 16.2%, methyl methacrylate 76.9%, methacrylic acid 5.4% and ethylene glycol dimethacrylate 1.5%.

Oxygen permeability (DK) was measured in a water/water cell using an O$_2$ Permeometer TM Model 101T. The units of DK are cm$^2$/sec (mlO$_2$/ml mmHg)×10$^{11}$.

TABLE II

| Example # | Copolymer based on | DK |
| --- | --- | --- |
| 11 | tris (pentamethyl disiloxy) silane-m,p-methacryloyloxymethyl phenylethane | 54 |
| 12 | tris (trimethylsiloxy) silane -m,p-methacryloxymethyl phenylethane | 18 |
| 13 | pentamethyldisiloxy-m,p-methacryloxymethyl phenylethane | 8 |
| 14 | bis (trimethylsiloxy) methyl-m,p-methacryloyloxymethyl phenylethane | 2.4 |

Example 15

Copolymerization of tris (trimethylsiloxy) silane(m,p-methacryloxymethyl)phenylethane with methyl methacrylate and methacrylic acid Tris (trimethylsiloxy) silane(m,p-methacryloxymethyl) phenylethane 3.84 g. was added to a clean, dry 20 ml glass, screw top test tube along with 3.62 g. methyl methacrylate, 0.39 g. methacrylic acid, 0.16 g. ethyleneglycol dimethacrylate and 0.09 g. USP 245. After degassing with Argon the tube was capped and placed in an oil bath at 50° C. for one hour and then at 70° C. for 72 hours. It was then carried through an annealing cycle at 120° C. A hard, transparent button was obtained that could be machined to a contact lens using standard lathing and polishing techniques. The contact lens thus obtained has a DK of 18.

The following table summarizes some of the monomers which have been or can be prepared in accordance with the invention.

TABLE III

| Compound Name | A | R | X | Y | Z | n |
| --- | --- | --- | --- | --- | --- | --- |
| tris(trimethylsiloxy)-silane-(m,p-methacryloxymethyl)-phenylethane | Ester | Methyl | —OSi(CH$_3$)$_3$ | * | —CH$_3$ | 1 |
| tris(pentamethyl disiloxyl silane-(m,p-methacryloxymethyl)phenylethane | Ester | Methyl | —OSi(CH$_3$)$_2$ | OSi(CH$_3$)$_3$* | —OSi(CH$_3$)$_3$ | 1 |
| tris(trimethylsiloxy)-silane-(m,p-N-methacrylaminomethyl)phenylethane | Amide | Methyl | —OSi(CH$_3$)$_3$ | * | —CH$_3$ | 1 |
| bis(trimethylsiloxy)methyl-silane-(m,p-N—methacrylaminomethyl)phenylethane | Amide | Methyl | —CH$_3$ | OSi(CH$_3$)$_3$ | —CH$_3$ | 1 |
| bis(trimethylsiloxy)methyl-silane-(m,p-methacryloxymethyl)phenylethane | Ester | Methyl | —CH$_3$ | OSi(CH$_3$)$_3$ | —CH$_3$ | 1 |
| trimethylsiloxy-dimethyl-silane-(m,p-methacryloxymethyl)phenylethane | Ester | Methyl | —CH$_3$ | * | —CH$_3$ | 1 |
| tris(pentamethyl disiloxyl silane-(m,p-3-N—methacryloxymethylureido-1-N—methyl)-phenylethane | Urea, m = 2 | Methyl | —OSi(CH$_3$)$_2$ | OSi(CH$_3$)$_3$* | —OSi(CH$_3$)$_3$ | 1 |

TABLE III-continued

| Compound Name | A | R | X | Y | Z | n |
|---|---|---|---|---|---|---|
| tris(trimethylsiloxy)-silane-(m,p-3-N—methacryl-oxymethylureido-1-N—methyl)-phenylethane | Urea, m-2 | Methyl | —OSi(CH₃)₃ | * | —CH₃ | 1 |
| bis(trimethylsiloxy)methyl-silane-(m,p-3-N—methacryl-oxymethylureido-1-N—methyl)-phenylethane | Urea, m = 2 | Methyl | —CH₃ | OSi(CH₃)₃ | —CH₃ | 1 |

*Y and X are the same.

Example 16

Films of the copolymers used in this example, which employ HFIS as the perfluoro styrene compound, were prepared in accordance with the details for preparation of films specified in earlier examples 11-14. In these instances, the siloxane monomer used in the copolymer combination was tris (trimethylsiloxy)-γ-methacryloxypropylsilane. A base copolymer was prepared that contained 30 parts of tris (trimethylsiloxy)-γ-methacryloxypropylsilane and 70 parts of methylmethacrylate. Added to this were respectively 5, 15 and 30 parts of HFIS and methacrylic acid (MA). The results are shown in Table III below.

TABLE IV**

|  | HFIS | | | NO COMONOMER | MA | | |
|---|---|---|---|---|---|---|---|
|  | 5 | 15 | 30 | 0 | 5 | 15 | 30 |
| DK | 8.8 | 8.2 | 8.9 | 9.3 | 7.7 | 6.0 | 5.1 |
| CONTACT ANGLE | 52° | 62° | 55° | 64° | 36° | 36° | — |
| TENSILE STRENGTH | 5,100 | 6,000 | 4,000 | 6,100 | 4,800 | — | 3,000 |
| MODULUS | 178,000 | 192,000 | 201,000 | 209,000 | 163,000 | — | 178,000 |

**Units of tensile strength and modulus are psi; DK units 10¹¹ MIO₂ cm²/sec ml MMHg at 35° C.

From these results it can be seen that the addition of up to 30% by weight of HFIS had no significant impact on the oxygen permeability of the siloxane copolymers. Methacrylic acid has the negative impact on oxygen permeability and causes haziness in concentrations above 15%. The trend of the data indicates that both methacrylic acid and HFIS will improve wettability but HFIS is a better comonomer than methacrylic acid in terms of oxygen permeability and mechanical properties. HFIS does act as a wetting monomer, on a more efficient basis than the conventionally used methacrylic acid and it does not adversely impact oxygen permeability as does methacrylic acid.

When the HFIS is substituted with other hydroxy-fluoroalkylstyrenes of the formula previously presented herein, substantially similar results are obtained in that excellent wettability is noted and no significant undesirable impact on oxygen permeability is noted.

Example 17

DK of Polymers Containing HFIS and Siloxanes

The following polymer compositions were made up in the manner previously described containing HFIS and the siloxanes shown by Formula I. Compositions 1, 2, and 3 shown below in the Table were made in the manner previously described in earlier examples. The DK, contact angle, and Tg were measured as shown in Table 5 below.

TABLE 5

|  | Comp. #1 | Comp. #2 | Comp. #3 |
|---|---|---|---|
| Penta Tris Styrene (Ex. 3) | 40 | 40 | 40 |
| Tris Urea (Ex. 6) | 28 | 18 | 12 |
| HFIS | 30 | 40 | 40 |
| MA | — | — | 6 |
| EGDMA | 2 | 2 | 2 |
| DK | 109 | 67 | 54 |
| CONTACT ANGLE | 26° | 20° | 17° |
| Tg | 100° | 113° | — |

All of the polymers that were prepared were brittle. Methacrylic acid was noted to significantly lower the contact angle, but adversely impacted oxygen permeability, and as well, had a significant negative impact on mechanical properties. As seen, the replacement of some of the siloxane, i.e. the penta tris styrene and the tris urea with some HFIS, significantly increased the Tg of the polymer. It can be concluded that the oxygen permability and the wettability of these polymers were exceptional.

Example 18

The following composition was prepared in accordance with the method described in Example 15. This composition represents the best current formulation known of compositions which contain both HFIS and a siloxane monomer. The composition was prepared in the manner previously described herein for the polymer compositions for making contact lenses.

| Composition | % |
|---|---|
| Penta Tris Styrene | 35 |
| Tris Urea | 10 |
| HFIS | 23 |
| MMA | 30 |
| EGDMA | 2 |

The properties of this composition were measured and found as follows:

| DK | 26 |
|---|---|
| Contact Angle | 35° |
| Tensile Strength | 2,100 |

-continued

| | |
|---|---|
| Elongation % | 1.8 |
| Modulus | 116,000 |
| Machineability | Acceptable |

The composition shown in this examples was used to make a contact lens. The lens made represented the best available combination of oxygen permeability and mechanical properties of any lens so far formulated. The properties were in every instance equivalent to or at least better than the claimed properties for materials currently under clinical investigation as hard gas permeable extended wear contact lenses.

It therefore can be seen that the invention accomplishes at least all of the stated objectives.

What is claimed is:

1. A copolymer for preparation of optical lenses which comprises a siloxane main monomer polymerizable to make a colorless, eye-inert polymer, said siloxane monomer having the formula:

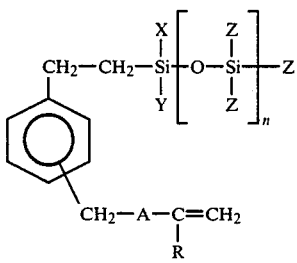

where
(1) "A" is selected from the group consisting of:

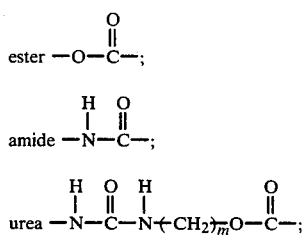

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

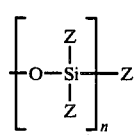

(5) Z is selected from the group consisting of $C_1$ to $C_5$ alkyl groups and phenyl groups; and
(6) n is an integer from zero to five; and from about 10% by weight to about 60% by weight of a hydroxyperfluoroalkylstyrene of the formula:

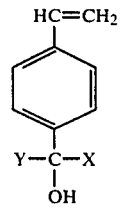

wherein X and Y are selected from the group consisting of monovalent perfluoralkyl, hydroperfluoroalkyl, and chloroperfluoroalkyl of up to 8 carbon atoms.

2. The copolymer composition of claim 1 wherein the alkyl moieties contain from $C_1$ to $C_3$.

3. The copolymer composition of claim 1 wherein the perfluroalkylstyrene is p-(2-hydroxyhexafluoroisopropyl)styrene.

4. A copolymer composition for preparation of optical lenses which comprises from about 25% by weight to about 50% of a siloxane monomer having the formula:

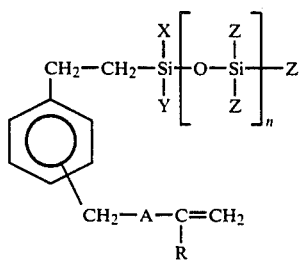

where
(1) "A" is selected from the group consisting of:

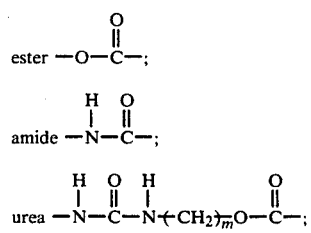

where m is a number and is from 2–4;
(2) R is hydrogen or methyl;
(3) X and Y are selected from the group consisting of $C_1$ to $C_5$ alkyl groups, phenyl groups and W groups;
(4) W is a group of the structure

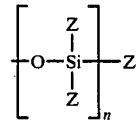

(5) Z is selected from the group consisting of $C_1$ to $C_5$ alkyl groups and phenyl groups; and
(6) n is an integer from zero to five; and from about 10% by weight to about 40% by weight of a hydroxyperfluoroalkylstyrene of the formula:

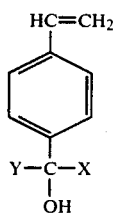

wherein X and Y are selected from the group consisting of monovalent perfluoroalkyl, hydroperfluoroalkyl, and chloroperfluoroalkyl of up to 8 carbon atoms.

5. The copolymer composition of claim 4 wherein the alkyl moieties contain from $C_1$ to $C_3$.

6. The copolymer composition of claim 4 wherein the perfluroalkylstyrene is p-(2-hydroxyhexafluoroisopropyl)styrene.

7. A gas permeable hard contact lens, shaped from a copolymer comprising from about 25% by weight to about 50% of a siloxane monomer having the formula:

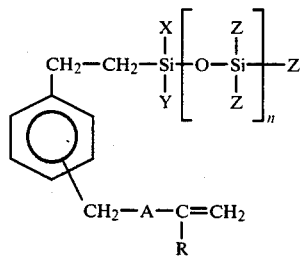

where
(1) "A" is selected from the group consisting of:

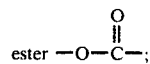

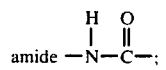

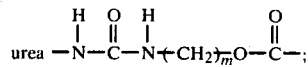

where m is a number and is from 2-4;
(2) R is hydrogen or methyl;
(3) X and Y are selected from the group consisting of $C_1$ to $C_5$ alkyl groups, phenyl groups and W groups;
(4) W is a group of the structure

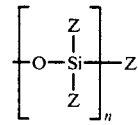

(5) Z is selected from the group consisting of $C_1$ to $C_5$ alkyl groups and phenyl groups; and
(6) n is an integer from zero to five; and from about 10% by weight to about 40% by weight of a hydroxyperfluoroalkylstyrene of the formula:

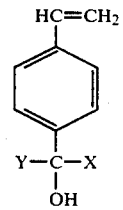

wherein X and Y are selected from the group consisting of monovalent perfluoroalkyl, hydroperfluoroalkyl, and chloroperfluoroalkyl of up to 8 carbon atoms.

* * * * *